(12) United States Patent
Megens et al.

(10) Patent No.: US 11,986,339 B2
(45) Date of Patent: May 21, 2024

(54) TRACKING AN INTERVENTIONAL DEVICE WITHIN AN ULTRASOUND IMAGE PLANE

(71) Applicant: KONINKLIJKE PHILIPS N.V., Eindhoven (NL)

(72) Inventors: Mischa Megens, Utrecht (NL); Hendrik Roelof Stapert, Eindhoven (NL); Mustafa Hakan Gokgurler, Helmond (NL); Stefan Van De Pas, Herten (NL); Jeroen Kortsmit, Son en Breugel (NL); Franciscus Hendrikus Van Heesch, Valkenswaard (NL); Harm Jan Willem Belt, Weert (NL); Ameet Kumar Jain, Boston, MA (US); Kunal Vaidya, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 17 days.

(21) Appl. No.: 17/266,599

(22) PCT Filed: Aug. 2, 2019

(86) PCT No.: PCT/EP2019/070920
§ 371 (c)(1),
(2) Date: Feb. 7, 2021

(87) PCT Pub. No.: WO2020/030557
PCT Pub. Date: Feb. 13, 2020

(65) Prior Publication Data
US 2021/0307717 A1 Oct. 7, 2021

Related U.S. Application Data

(60) Provisional application No. 62/716,088, filed on Aug. 8, 2018.

(30) Foreign Application Priority Data

Oct. 5, 2018 (EP) .................................... 18198801

(51) Int. Cl.
*A61B 8/08* (2006.01)
*A61B 8/00* (2006.01)
(Continued)

(52) U.S. Cl.
CPC .............. *A61B 8/0841* (2013.01); *A61B 8/12* (2013.01); *A61B 8/4245* (2013.01);
(Continued)

(58) Field of Classification Search
CPC ....... A61B 8/0841; A61B 8/12; A61B 8/4245; A61B 8/4477; A61B 8/4483; A61B 8/5207; A61B 2017/3413
See application file for complete search history.

(56) References Cited

U.S. PATENT DOCUMENTS

2008/0221446 A1* 9/2008 Washburn ............ A61B 8/4254
600/437
2010/0298704 A1* 11/2010 Pelissier .............. A61B 8/0841
600/443
(Continued)

FOREIGN PATENT DOCUMENTS

WO 2011138698 A1 11/2011
WO 2015101949 A1 7/2015
(Continued)

OTHER PUBLICATIONS

International Search Report and Written Opinion of PCT/EP2019/070920, dated Aug. 29, 2019.

*Primary Examiner* — Joseph M Santos Rodriguez
*Assistant Examiner* — Maria Christina Talty

(57) ABSTRACT

System (10) for determining a position of an interventional device (11) respective an image plane (12) defined by an
(Continued)

ultrasound imaging probe (13). The position is determined based on ultrasound signals transmitted between the ultrasound imaging probe (13) and an ultrasound transducer (15) attached to the interventional device (11). An image reconstruction unit (IRU) provides a reconstructed ultrasound image (RUI). A position determination unit (PDU) computes a lateral position ($LAP_{TOFSmax, \theta_{IPA}}$) of the ultrasound transducer (15) respective the image plane (12) based on a time of flight ($TOF_{Smax}$) of a maximum detected intensity ($I_{Smax}$) ultrasound signal. The position determination unit (PDU) also computes an out-of-plane distance ($D_{op}$) between the ultrasound transducer (15) and the image plane (12). Computing the out-of-plane distance ($D_{op}$) involves comparing the maximum detected intensity ($I_{Smax}$) with a model (MO) describing an expected variation of in-plane maximum detected intensity ($I_{SmaxInplane}$) with time of flight.

20 Claims, 4 Drawing Sheets

(51) Int. Cl.
*A61B 8/12* (2006.01)
*A61B 17/34* (2006.01)

(52) U.S. Cl.
CPC .......... *A61B 8/4477* (2013.01); *A61B 8/4483* (2013.01); *A61B 8/5207* (2013.01); *A61B 2017/3413* (2013.01)

(56) References Cited

U.S. PATENT DOCUMENTS

| | | | |
|---|---|---|---|
| 2012/0321154 A1* | 12/2012 | Korsten | A61B 8/0841 382/128 |
| 2016/0038119 A1* | 2/2016 | Desjardins | A61B 8/4444 600/424 |
| 2016/0324501 A1* | 11/2016 | Vignon | A61B 8/4477 |
| 2016/0367322 A1* | 12/2016 | Jain | G01S 15/899 |
| 2017/0100101 A1* | 4/2017 | Ryoo | A61B 8/5207 |
| 2017/0202625 A1* | 7/2017 | Bharat | A61B 8/12 |
| 2019/0167354 A1* | 6/2019 | Heaney | A61B 34/20 |

FOREIGN PATENT DOCUMENTS

| | | | | |
|---|---|---|---|---|
| WO | 2016009350 A1 | | 1/2016 | |
| WO | WO-2017102369 A1 | * | 6/2017 | ......... A61B 17/3403 |
| WO | 2018060499 A1 | | 4/2018 | |

* cited by examiner

This application is the U.S. National Phase application under 35 U.S.C. § 371 of International Application No. PCT/EP2019/070920, filed on Aug. 2, 2019, which claims the benefit of U.S. Provisional Patent Application Ser. No. 62/716088, filed Aug. 8, 2018 and European Patent Application No. 18198801.5, filed on Oct. 5, 2018. These applications are hereby incorporated by reference herein.

TRACKING AN INTERVENTIONAL DEVICE WITHIN AN ULTRASOUND IMAGE PLANE

CROSS-REFERENCE TO PRIOR APPLICATION

FIELD OF THE INVENTION

The invention relates to determining a position of an interventional device respective an image plane of a beamforming ultrasound imaging probe.

BACKGROUND OF THE INVENTION

Interventional devices such as medical needles, catheters and surgical tools are often difficult to visualize in an ultrasound image due to the specular nature of their reflectivity, particularly at unfavorable incidence angles.

In this respect documents WO2011138698A1, WO2015101949A1 and WO2016009350A1 describe systems for tracking an instrument in an ultrasound field with an ultrasound receiver that is mounted to the instrument. The position of the ultrasound receiver is subsequently displayed in an ultrasound image corresponding to the ultrasound field.

A document U.S. 2016/038119 A1 relates to an ultrasound system comprising an ultrasound unit including: an ultrasound probe for acquiring an anatomical image of a human body and for locating a medical instrument with respect to said image, the ultrasound probe including a first set of imaging transducer elements and a second set of localisation transducer elements, wherein the first set of imaging transducer elements are distinct and disjoint from the second set of localisation transducer elements, wherein: the first set of imaging transducer elements are configured to: produce ultrasound imaging transmissions into the human body, wherein the ultrasound imaging transmissions are focussed into an image scan plane, and receive reflections of the ultrasound imaging transmissions for generating a two-dimensional anatomical image corresponding to the image scan plane; and wherein the second set of localisation transducer elements are configured to produce ultrasound localisation transmissions into the human body for locating the medical instrument with respect to the anatomical image, wherein the ultrasound localisation transmissions extend outside the image scan plane, and wherein at least two transducer elements from said second set are spaced from one other in a direction perpendicular to the image scan plane; and a sensor console for receiving the signals from said transducer that correspond to the localisation transmissions; wherein the ultrasound system is configured to process the received signals to determine the location of the medical instrument within the human body relative to the ultrasound probe based on the received signals.

Another document U.S. 2017/202625 A1 relates to a system for tracking an instrument. The system includes two or more sensors disposed along a length of an instrument and being spaced apart from adjacent sensors. An interpretation module is configured to select and update an image slice from a three-dimensional image volume in accordance with positions of the two or more sensors. The three-dimensional image volume includes the positions two or more sensors with respect to a target in the volume. An image processing module is configured to generate an overlay indicating reference positions in the image slice. The reference positions include the positions of the two or more sensors and relative offsets from the image slice in a display to provide feedback for positioning and orienting the instrument.

However, when the ultrasound receiver in such systems lies outside the image plane, i.e. is "out-of-plane", determination of the ultrasound receiver's position, and ultimately that of the interventional device can be challenging.

In this respect, document WO2018060499A1 describes a system for indicating a position of an interventional device feature of an interventional device respective an image plane defined by an ultrasound imaging probe of a beamforming ultrasound imaging system in which the position of the interventional device feature is determined based on ultrasound signals transmitted between the ultrasound imaging probe and an ultrasound transducer attached to the interventional device at a predetermined distance from the interventional device feature. An icon providing unit provides a first icon indicative of a circular zone with a radius corresponding to the predetermined distance. The first icon is displayed in a fused image that includes a reconstructed ultrasound image from the beamforming ultrasound imaging system. In this document an out-of-plane distance is computed based on a model of the variation in signal intensity with out-of-plane distance $D_{op}$ for the determined range.

Despite these solutions there remains room for improved techniques for determining a position of an interventional device respective an ultrasound imaging plane.

SUMMARY OF THE INVENTION

In seeking to provide improved tracking of an interventional device, a system for determining a position of an interventional device respective an image plane defined by an ultrasound imaging probe of a beamforming ultrasound imaging system is provided in which the position of the interventional device is determined based on ultrasound signals transmitted between the ultrasound imaging probe and an ultrasound transducer attached to the interventional device. The system includes an image reconstruction unit and a position determination unit. The image reconstruction unit provides a reconstructed ultrasound image corresponding to an image plane defined by the ultrasound imaging probe. The position determination unit computes a lateral position of the ultrasound transducer respective the image plane based on a time of flight of a maximum detected intensity ultrasound signal transmitted between the ultrasound imaging probe and the ultrasound transducer. The position determination unit also computes an out-of-plane distance between the ultrasound transducer and the image plane, based on the intensity and the time of flight of the maximum detected intensity ultrasound signal. Computing the out-of-plane distance includes comparing the maximum detected intensity with a model describing an expected variation of in-plane maximum detected intensity with time of flight, at the time of flight of the maximum detected intensity ultrasound signal. The position determination unit subsequently indicates the out-of-plane distance in the reconstructed ultrasound image.

The model used in computing the out-of-plane distance thus describes an expected variation of in-plane maximum detected intensity with time of flight. The in-plane detected intensity may exhibit low variability between different ultrasound imaging probes and thus the same model may be used for ultrasound imaging probes of the same type. Moreover, this model requires only one-dimensional calibration data; i.e. a variation in the intensity with time of flight, and this requires only a limited amount of calibration data. Moreover, in-use the out-of-plane distance may be determined with low latency due to the need to search in only one, i.e. the time of flight, dimension.

In accordance with one aspect, indicating the out-of-plane distance includes providing a first icon at the computed lateral position, the first icon being indicative of a circular zone with a radius corresponding to the out-of-plane distance. The use of an icon at the computed position with a circular zone indicative of the out-of-plane distance indicates intuitively to a user whether the interventional device is being advanced towards or away-from the image plane based on whether the circle grows or shrinks This allows for improved guidance of the interventional device.

In accordance with another aspect the radius corresponding to the out of plane distance is determined based on scaling the maximum detected intensity to the expected in-plane maximum detected intensity, at the time of flight of the maximum detected intensity ultrasound signal. The maximum detected intensity typically reduces as the out-of-plane distance $D_{op}$ is increased. However the nature of this variation with out-of-plane distance may depend upon the time of flight; in other words the range between the ultrasound imaging probe and the ultrasound detector. Determining the radius based on scaling the maximum detected intensity to the expected in-plane maximum detected intensity results in a qualitative indication of the out-of-plane distance. Such an indication provides adequate feedback for a user to accurately navigate the interventional device to the image plane, and obviates the need for full three-dimensional calibration data that might otherwise be required to determine an exact out-of-plane distance, as well as the latency associated with searching such three-dimensional data to determine the out of-plane distance.

In accordance with another aspect the first icon includes a perimeter. The appearance of the first icon is configured to change based on a comparison of the maximum detected intensity with the expected in-plane maximum detected intensity, at the time of flight of the maximum detected intensity ultrasound signal, if i) a ratio of the maximum detected intensity to the expected in-plane maximum detected intensity, at the time of flight of the maximum detected intensity ultrasound signal, or ii) the maximum detected intensity, lies within a predetermined range. Changing the appearance of the perimeter has the effect of indicating to a user the position of the interventional device at predetermined positions respective the imaging plane. This feature allows the rapid indication to a user of the general position of the interventional device respective the imaging plane. For example, the color of the icon may be green when the maximum detected intensity or its ratio indicates a value close to the expected in-plane maximum detected intensity, and red when for values within an abutting range, and white for positions outside this range. This indicates quickly to a user whether the interventional device is currently in-plane.

In accordance with another aspect the radius corresponding to the out of plane distance has a minimum value. The position determination unit limits the radius to the minimum value if i) a ratio of the maximum detected intensity to the expected in-plane maximum detected intensity, at the time of flight of the maximum detected intensity ultrasound signal, or ii) the maximum detected intensity, exceeds a predetermined value. A user is typically interested in positioning the interventional device in the imaging plane; and thus in this implementation the icon may for example change when the icon is within a predetermined range of exactly in the imaging plane. In so doing the user may to some extent relax their concentration when the interventional device is sufficiently well localized. This prevents the user from continually making minute adjustments of the position of the interventional device, allowing them to focus on other tasks.

In accordance with another aspect the position determination unit suppresses the provision of the first icon in the reconstructed ultrasound image if i) a ratio of the maximum detected intensity to the expected in-plane maximum detected intensity, at the time of flight of the maximum detected intensity ultrasound signal, or ii) the maximum detected intensity, falls below a predetermined value. If either of these parameters fall below the predetermined value the system may be insufficiently sensitive to reliably indicate the position of the interventional device respective the imaging plane. Weakly detected ultrasound signals may be confounded by electromagnetic interference or noise. Under such circumstances it is preferable to suppress the provision of the first icon in the reconstructed ultrasound image in order to avoid indicating a potentially inaccurate position.

In accordance with another aspect the interventional device includes a feature, such as its distal end. The ultrasound transducer is attached to the interventional device at a predetermined distance from the interventional device feature. The position determination unit also provides a second icon in the reconstructed ultrasound image, the second icon being indicative of a circular zone with a radius corresponding to the predetermined distance between the ultrasound transducer and the interventional device feature. The first icon and the second icon share a common center, i.e. at the computed lateral position. The second icon is indicative of a range of possible positions of the feature, e.g. the distal end, of the interventional device. Providing both icons in the reconstructed ultrasound image beneficially indicates the position of the feature of the interventional device respective the image plane. Two extreme scenarios are now explained in order to indicate the benefits of providing both icons.

In a first scenario the interventional device feature and the ultrasound transducer both lie in the image plane. The reconstructed ultrasound image includes the first icon which indicates the out-of-plane position and is centered at the position of the ultrasound transducer. The first icon indicates, as described above, that the transducer is in the image plane. The interventional device feature lies somewhere around the perimeter of the circular zone indicated by the overlapping second icon; this being because the radius of the circular zone corresponds to the predetermined distance between the ultrasound transducer and the interventional device feature. Thus during an in-plane procedure, when the circles overlap, the perimeter of the icons indicates the position of the interventional device feature. Based on the user's progression of the needle and its approximate trajectory, the user will also know approximately which part of the perimeter of the circular zone the distal end of the medical needle is actually located. Moreover the user will be aware of this trajectory from intermittent reconstructed ultrasound images of the shaft of medical needle 11. Thus the user can mentally augment the information provided by the first icon in order to identify more precisely where on the perimeter of the circular zone the interventional device feature lies.

In a second scenario the interventional device feature lies in the image plane and the ultrasound transducer lies above or below the image plane along a line passing through the feature and normally with respect to the image plane. Here the reconstructed ultrasound image includes the first icon which is centered at the position of the ultrasound transducer as-projected onto the image plane. Such a projection can involve i) projecting the position of the ultrasound transducer in a direction that is normal to the image plane, or ii) projecting a range between the ultrasound imaging probe and the ultrasound transducer onto the image plane, or iii) projecting the position of the ultrasound transducer in a direction that is perpendicular to the range between the ultrasound imaging probe and the ultrasound transducer. The first icon indicates the out-of-plane distance. Due to the normal positioning of the ultrasound transducer respective the ultrasound image plane, the center of the second icon indicates the position of the feature, i.e. the distal end, of the interventional device. When the first and second icons overlap, i.e. they indicate the same distance, the interventional device feature has just reached the image plane.

In intermediate scenarios the interventional device feature lies somewhere between the center of the circular zone indicated by the second icon and the perimeter of its circular zone.

Because the interventional device feature is known to be on or within the perimeter of the circular zone defined by the second icon, improved positioning of the interventional device feature respective the image plane is provided. Put another way, a user of the system has confidence that the interventional device feature does not impact image features that lie outside this circular zone. Advantageously the localization can be provided using only a single ultrasound transducer, thereby simplifying manufacture of the interventional device.

In accordance with another aspect the position determination causes the appearance of at least one of the first icon and the second icon to change when the out-of-plane distance is less than or equal to the predetermined distance. In so doing, during the aforementioned out-of-plane procedure, a user is alerted to the fact that the interventional device feature is in the center of the image plane.

In accordance with another aspect the radius of the first icon has a minimum value that is equal to the radius of the second icon, and wherein the radius of the first icon is limited to the minimum value when the out-of-plane distance is less than or equal to the predetermined distance. By so limiting the size of the first icon as the interventional device approaches the image plane, as described above, in an out-of-plane procedure a user may to some extent relax their concentration when the minimum size is reached knowing that, sufficient positioning accuracy has been reached.

In accordance with other aspects a method and corresponding computer program product that may be used in conjunction with the system are provided.

It is to be noted that the various aspects described in relation to the system may be combined to provide further advantageous effects. Moreover, aspects of the system may be used interchangeably with the method, and vice versa.

BRIEF DESCRIPTION OF THE FIGURES

FIG. 5A, FIG. 5B, FIG. 5C each illustrate a reconstructed ultrasound image RUI that includes a region of interest ROI, first icon $C_{op}$ and a co-centred second icon $C_{de}$ that is indicative of a circular zone with a radius corresponding to distance $L_p$ between ultrasound transducer 15 and interventional device feature 11a.

DETAILED DESCRIPTION OF THE INVENTION

In order to illustrate the principles of the present invention, various systems are described in which the position of an interventional device, exemplified by a medical needle, is indicated respective an image plane defined by a linear array of a 2D ultrasound imaging probe. Moreover, in some examples the position of a feature, such as the distal end, of the medical device is also tracked.

It is however to be appreciated that the invention also finds application with other interventional devices such as, and without limitation, a catheter, a guidewire, a probe, an endoscope, an electrode, a robot, a filter device, a balloon device, a stent, a mitral clip, a left atrial appendage closure device, an aortic valve, a pacemaker, an intravenous line, a drainage line, a surgical tool, a tissue sealing device, a tissue cutting device or an implantable device. The tracked feature of such interventional devices may exemplarily include a distal end of the interventional device, a biopsy sampling point of the interventional device, a cutting edge of the interventional device, an opening of a channel in the interventional device, a sensor (e.g. for sensing flow, pressure, temperature etc.) of the interventional device, a surgical tool (e.g. a scraper) integrated in the interventional device, a drug delivery point of the interventional device, or an energy delivery point of the interventional device.

Furthermore it is to be appreciated that the exemplified linear array of a 2D ultrasound imaging probe is only one example of an ultrasound transceiver array of a beamforming ultrasound imaging system in which the invention may be used. The invention also finds application in other types of beamforming ultrasound imaging systems whose associated ultrasound transceiver arrays exemplarily include a 2D array of a 3D imaging probe (or in bi-plane view), a "TRUS" transrectal ultrasonography probe, an "IVUS" intravascular ultrasound probe, a "TEE" transesophageal probe, a "TTE" transthoracic probe, a "TNE" transnasal probe, an "ICE" intracardiac probe.

Figure 1:
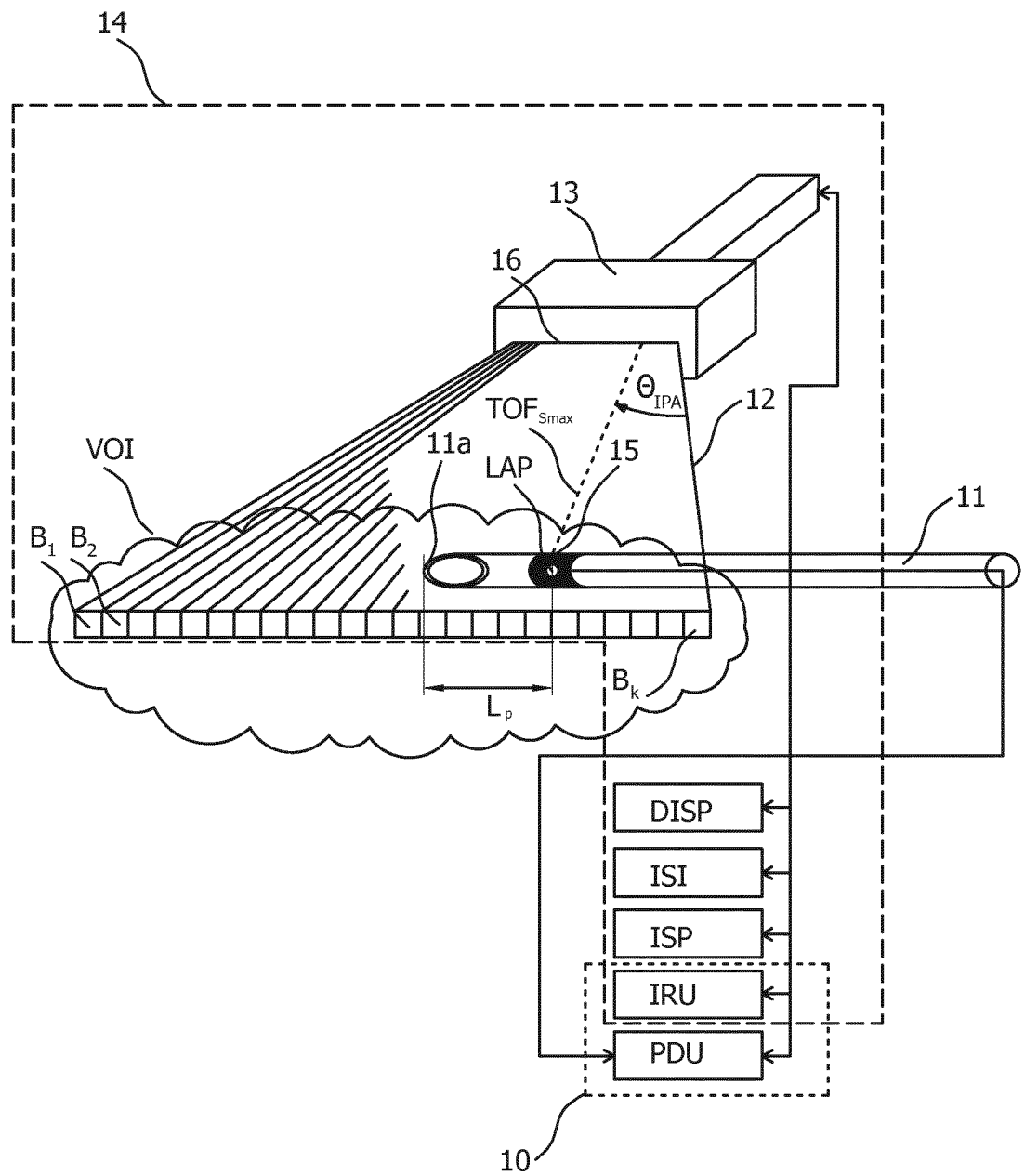
FIG. 1 illustrates a beamforming ultrasound imaging system 14 in combination with an in-plane interventional device 11 and an embodiment of the invention in the form of system 10.

FIG. 1 illustrates a beamforming ultrasound imaging system 14 in combination with an in-plane interventional device 11 and an embodiment of the invention in the form of system 10. In FIG. 1, beamforming ultrasound imaging system 14 includes a 2D ultrasound imaging probe 13 which is in communication with image reconstruction unit IRU, imaging system processor ISP, imaging system interface ISI and display DISP. The units IRU, ISP, ISI and DISP are conventionally located in a console that is in wired communication with 2D ultrasound imaging probe 13. It is also contemplated that wireless communication, for example using an optical, infrared, or an RF communication link, may replace the wired link. It is also contemplated that some of units IRU, ISP, ISI and DISP may instead be incorporated within 2D ultrasound imaging probe 13, as in for example the Philips Lumify ultrasound imaging system. In FIG. 1, 2D ultrasound imaging probe 13 includes linear ultrasound transceiver array 16 that transmits and receives ultrasound energy within an ultrasound field that intercepts volume of interest VOI. The ultrasound field is fan-shaped in FIG. 1 and includes multiple ultrasound beams $B_{1 \ldots k}$ that define image plane 12. Note that a fan-shaped beam is illustrated in FIG. 1 for the purposes of illustration only and that the invention is not limited to a particular shape of ultrasound field. Beamforming ultrasound imaging system 14 may also include electronic driver and receiver circuitry, not shown, that is configured to amplify and/or to adjust the phase of signals transmitted by or received by 2D ultrasound imaging probe 13 in order to generate and detect ultrasound signals in beams $B_{1 \ldots k}$. The electronic driver and receiver circuitry may thus be used to steer the emitted and/or received ultrasound beam direction.

In-use, beamforming ultrasound imaging system 14 is operated in the following way. An operator may plan an ultrasound procedure via imaging system interface ISI. Once an operating procedure is selected, imaging system interface ISI triggers imaging system processor ISP to execute application-specific programs that generate and interpret the signals transmitted by and detected by 2D ultrasound imaging probe 13. Beamforming ultrasound imaging system 14 may also include a memory (not shown) for storing such programs. The memory may for example store ultrasound beam control software that is configured to control the sequence of ultrasound signals transmitted by and/or received by ultrasound imaging probe 13. Image reconstruction unit IRU, which may alternatively form part of imaging system processor ISP, reconstructs data received from the ultrasound imaging probe 13 into an image corresponding to image plane 12 and which thus intercepts volume of interest VOI, and subsequently displays this image on display DISP. A planar section through volume of interest VOI is termed region of interest ROI herein. Reconstructed ultrasound image RUI may thus include region of interest ROI. The reconstructed image may for example be an ultrasound Brightness-mode "B-mode" image, otherwise known as a "2D mode" image, a "C-mode" image or a Doppler mode image, or indeed any ultrasound planar image.

Also shown in FIG. 1 is a medical needle 11 as an example of an interventional device, and an embodiment of the invention, system 10, that may be used to indicate a position of interventional device 11, i.e. the medical needle, respective image plane 12 of ultrasound imaging probe 13. This embodiment, system 10, includes image reconstruction unit IRU and position determination unit PDU. These units are in communication with one another as illustrated by the interconnecting arrows. It is also contemplated that one or more of units PDU, IRU may be incorporated within a memory or a processor of beamforming ultrasound imaging system 14, for example within a memory or a processor that also provides the functionality of unit ISP. Medical needle 11 that is tracked, includes ultrasound transducer 15 that may be positioned at predetermined distance $L_p$ from distal end 11a of interventional device 11.

In-use, a position of interventional device 11, or more specifically that of ultrasound transducer 15 attached thereto, is computed respective image plane 12 by position determination unit PDU based on ultrasound signals transmitted between ultrasound transceiver array 16 and ultrasound transducer 15.

In one configuration ultrasound transducer 15 is a detector that receives ultrasound signals corresponding to beams $B_{1 \ldots k}$. Position determination unit PDU identifies the lateral position LAP of ultrasound transducer 15 respective image plane 12 by correlating; i.e. comparing, the ultrasound signals emitted by ultrasound transceiver array 16 with the ultrasound signals detected by ultrasound transducer 15. More specifically this correlation determines the best fit position of ultrasound transducer 15 respective image plane 12 based on i) the intensities of the ultrasound signals corresponding to each beam $B_{1 \ldots k}$ that are detected by ultrasound transducer 15 and ii) based on the time delay, i.e. time of flight, between emission of each beam $B_{1 \ldots k}$ and its detection by ultrasound transducer 15. This may be illustrated as follows. When ultrasound transducer 15 is in the vicinity of image plane 12, ultrasound signals from the nearest of beams $B_{1 \ldots k}$ to the transducer will be detected with a relatively larger intensity whereas more distant beams will be detected with relatively smaller intensities. Typically the beam that is detected with the maximum detected intensity is identified as the one that is closest to ultrasound detector 15. In other words, the maximum detected intensity $I_{Smax}$ ultrasound signal identifies the in-plane angle $\Theta_{IPA}$ between ultrasound transceiver array 16 and ultrasound transducer 15. The time of flight, between the emission of this beam (from beams $B_{1 \ldots k}$) and its subsequent detection is indicative of the range between ultrasound transceiver array 16 and ultrasound transducer 15. Thus the time delay of the ultrasound signal in the beam that was detected with maximum detected intensity, $I_{Smax}$, i.e. $TOF_{Smax}$, is the ultrasound signal that is selected from the ultrasound signals of all beams. Since the time of flight is indicative of the range, in polar coordinates the lateral position of ultrasound transducer 15 respective image plane 12 may be represented by $LAPT_{TOFSmax, \Theta_{IPA}}$. If desired, the range may be determined by multiplying the time delay by the speed of ultrasound propagation.

In another configuration ultrasound transducer 15 is an emitter that emits one or more ultrasound pulses. Such pulses may for example be emitted during tracking frames that are interleaved between the usual imaging frames of ultrasound imaging system 14. In such a tracking frame the ultrasound transceiver array 16 may be operated in a receive-only mode in which it listens for ultrasound signals originating from the vicinity of image plane 12. Ultrasound transceiver array 16 is thus configured as a one-way receive-only beamformer. Position determination unit PDU identifies from which beam of beams $B_{1 \ldots k}$ the pulse(s) originated based on the ultrasound signals emitted by ultrasound transducer 15 and those detected by ultrasound transceiver array 16. As in the configuration above, position determination unit PDU may use a correlation procedure that, based on the ultrasound signal detected with maximum intensity and its time of flight, identifies the closest beam and thus the point at which the ultrasound signal was emitted, i.e. its lateral position $LAP_{TOFSmax, \Theta_{IPA}}$ in the same manner. Thus, when ultrasound transducer 15 is an emitter, a correlation, i.e. comparison, procedure may again be used to determine its best-fit position respective image plane 12 for each tracking frame.

In another configuration ultrasound transducer 15 may be configured to act as both a receiver and an emitter, or include both a receiver and an emitter. In this configuration ultrasound transducer 15 may be triggered to emit one or more ultrasound pulses upon receipt of an ultrasound signal from ultrasound transceiver array 16; optionally following a delay that is equal to one or more frame periods of ultrasound imaging system 14. In this way the pulse(s) emitted by ultrasound transducer 15 during an imaging mode are received by ultrasound transceiver array 16 in the form of an echo in the reconstructed ultrasound at an in-plane angular position, i.e. in an image line, that corresponds to the triggering beam $B_{1...k}$. Ultrasound transducer 15 thus appears as a bright spot in the reconstructed image. Position determination unit PDU may subsequently identify this bright spot in the reconstructed image and thus again compute a lateral position $LAP_{TOFSmax, \theta IPA}$ of ultrasound transducer 15 respective image plane 12.

In yet another configuration, not illustrated, ultrasound imaging probe 13 may further include at least three ultrasound emitters that are attached to the ultrasound imaging probe 13. The at least three ultrasound emitters are in communication with position determination unit PDU. Moreover the position determination unit PDU is configured to compute a position of the ultrasound transducer 15 respective the image plane 12 based on ultrasound signals transmitted between the at least three ultrasound emitters attached to the ultrasound imaging probe 13, and the ultrasound transducer 15. In this configuration position determination unit PDU determines a range between each emitter and ultrasound transducer 15 based on the time of flight of ultrasound signals emitted by each emitter. The three dimensional position of ultrasound transducer 15 is subsequently determined using triangulation. This provides the position of ultrasound transducer 15 in three dimensions respective ultrasound imaging probe 13, or more specifically respective image plane 12 since the at least three emitters are attached to the ultrasound imaging probe 13. The three-dimensional position may subsequently be mapped to image plane 12 and thus again represented by $LAP_{TOFSmax, \theta IPA}$. Ultrasound emitters are preferred in this configuration because the supply of high power ultrasound signals to the emitters, necessary for accurate positioning over a large range, is simpler when the emitters are proximate ultrasound imaging probe 13 where a power source is readily available. This arrangement is thus preferred in contrast to locating a high power emitter on interventional device 11. In-use, the lateral position of interventional device 11, or more specifically that of ultrasound transducer 15 attached thereto, is thus again computed respective image plane 12 by position determination unit PDU based on ultrasound signals transmitted between the at least three emitters and ultrasound transducer 15.

In summary, in this in-plane arrangement in which ultrasound transducer 15 is in the image plane, position determination unit PDU illustrated in FIG. 1 may be used in any of the above configurations to compute a lateral position of ultrasound transducer 15 respective image plane 12 based on ultrasound signals transmitted between ultrasound imaging probe 13 and ultrasound transducer 15.

Figure 2:
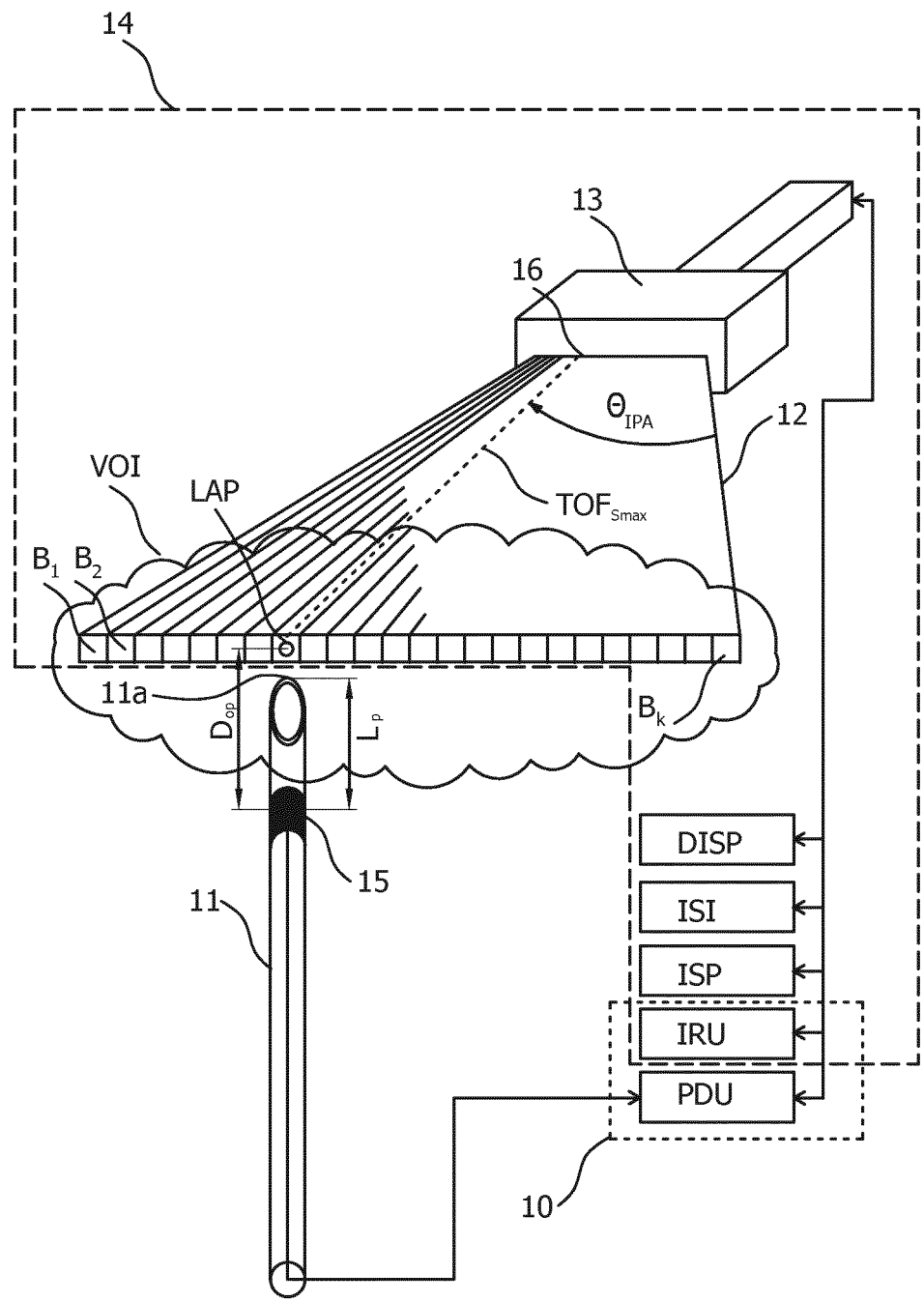
FIG. 2 illustrates a beamforming ultrasound imaging system 14 in combination with an interventional device 11 disposed at an out-of-plane distance $D_{op}$ and an embodiment of the invention in the form of system 10.

When ultrasound transducer 15 is disposed away from the image plane, i.e. out-of-plane, the same procedure may be used to determine a lateral position of ultrasound transducer 15, i.e. a position projected onto image plane 12. An additional procedure that uses the intensity, $I_{Smax}$, and the time of flight, $TOF_{Smax}$, of the maximum detected intensity $I_{Smax}$ ultrasound signal, is also used to estimate a distance of ultrasound transducer 15 from image plane 12. In this respect, FIG. 2 illustrates a beamforming ultrasound imaging system 14 in combination with an interventional device 11 disposed at an out-of-plane distance pop and an embodiment of the invention in the form of system 10. Although beams $B_{1...k}$ of ultrasound imaging probe 13 are illustrated as being in plane 12, this plane has a finite thickness and a reduced ultrasound signal is typically detectable for small out-of-plane displacements. These signals are used in the present invention to estimate the out-of-plane distance $D_{op}$ of ultrasound transducer 15.

Figure 3:
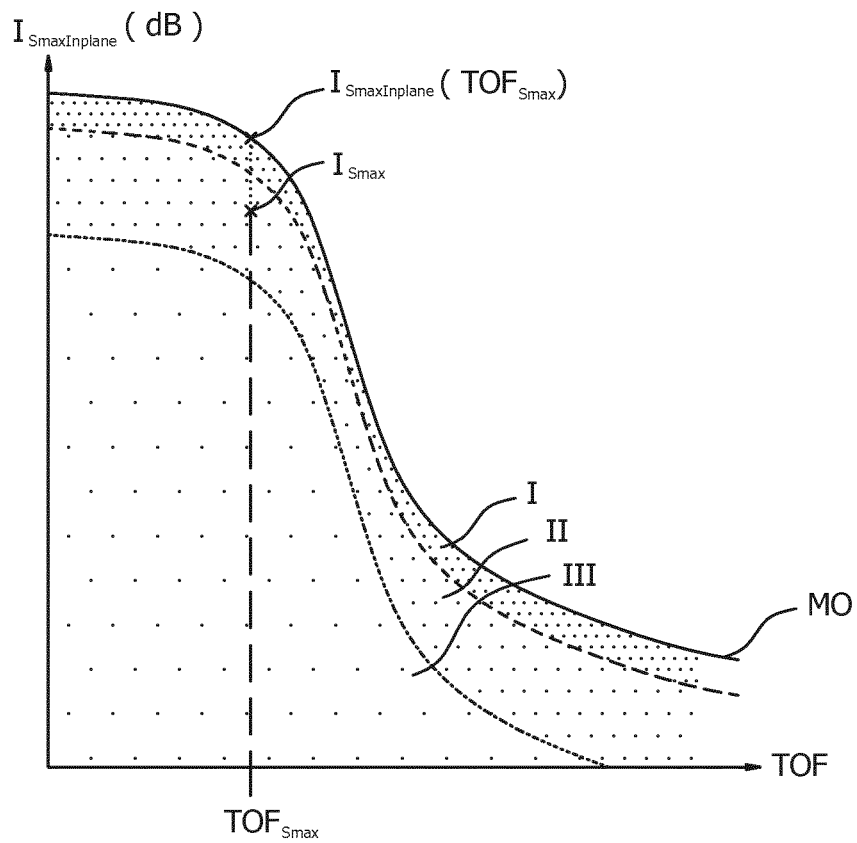
FIG. 3 illustrates a model MO describing an expected variation of in-plane maximum detected intensity, $I_{SmaxInplane}$ (dB) with time of flight, TOF.

Thereto, FIG. 3 illustrates a model MO describing an expected variation of in-plane maximum detected intensity, $I_{SmaxInplane}$ (dB) with time of flight, TOF. Model MO, indicated by the solid curve, illustrates that as the time of flight TOF, i.e. the depth into tissue increases, the in-plane maximum detected intensity, $I_{SmaxInplane}$, of detected ultrasound signals initially decreases slowly, then more rapidly, and then more slowly again. The shape of the model is affected by attenuation of ultrasound signals and may be determined from theoretical calculations or empirical measurements of the in-plane maximum intensity obtained in tissue or corresponding matter. Model MO depends only on time of flight and is invariant with in-plane angle $\theta_{IPA}$. It is noted that model MO does not model the maximum detected intensity, $I_{SmaxInplane}$ as a function of out-of-plane distance. Consequently model MO requires only a limited amount of, i.e. one-dimensional, calibration data. In contrast to e.g. a three-dimensional model, in-use the out-of-plane distance may be determined with model MO with low latency due to the need to search in only one, i.e. time of flight, dimension. The modeled in-plane maximum detected intensity, $I_{SmaxInplane}$ has been found to reliably represent different beamforming ultrasound imaging probes of the same type, which means that the same model may be used for beamforming ultrasound imaging probes of the same type.

With reference to FIG. 2 and FIG. 3, in-use, computing out-of-plane distance $D_{op}$ comprises comparing the maximum detected intensity $I_{Smax}$ with model MO. The out-of-plane distance $D_{op}$ may subsequently be indicated in reconstructed ultrasound image RUI. The out-of-plane distance may be indicated numerically for example, or as a size or color of an icon that varies accordance with $D_{op}$.

Comparing the maximum detected intensity $I_{Smax}$ with model MO may for instance involve determining a difference or ratio between detected intensity $I_{Smax}$ and the in-plane maximum detected intensity, $I_{SmaxInplane}$ at the time of flight $TOF_{Smax}$ corresponding to the computed lateral position $LAP_{TOFSmax}$. In one exemplary implementation the maximum detected intensity $I_{Smax}$ at the computed lateral position $LAP_{TOFSmax, \theta IPA}$ of the ultrasound transducer may thus be scaled to the in-plane maximum detected intensity $I_{SmaxInplane}$, at the time of flight $TOF_{Smax}$ corresponding to the computed lateral position $LAP_{TOFSmax, \theta IPA}$. A qualitative indication of the out-of-plane distance may subsequently be indicated in reconstructed ultrasound image RUI. For example, an icon may be displayed that has a size that varies in accordance with:

$$\text{Size} = k_1 + k_2 \cdot \left(1 - \frac{I_{Smax}}{I_{SmaxInplane}}\right) \quad \text{Equation 1}$$

and wherein $k_1$ and $k_2$ are constants and $k_1$ may include zero.

In another exemplary implementation, with reference to FIG. 3, the color of an icon may be configured to change based on the value of the maximum detected intensity $I_{Smax}$ in relation to $I_{SmaxInplane}$, at the time of flight $TOF_{Smax}$. For example, with reference to FIG. 3; zones I, II, and III, which represent predetermined ranges of $I_{Smax}$ or predetermine ranges of its ratio in relation to $I_{SmaxInplane}$, may define different colors of an icon displayed in the reconstructed ultrasound image, each color being applied to the icon when the maximum detected intensity $I_{Smax}$ lies in the respective range.

Thus, in summary, and with reference to FIG. 1-FIG. 3, a system 10 for indicating a position of an interventional device 11 respective an image plane 12 defined by an ultrasound imaging probe 13 of a beamforming ultrasound imaging system 14 in which the position of the interventional device 11 is determined based on ultrasound signals transmitted between the ultrasound imaging probe 13 and an ultrasound transducer 15 attached to the interventional device 11, includes:

image reconstruction unit IRU that provides reconstructed ultrasound image RUI corresponding to image plane 12 defined by ultrasound imaging probe 13; and position determination unit PDU that:
computes lateral position $LAP_{TOFSmax, \theta IPA}$ of ultrasound transducer 15 respective image plane 12 based on a time of flight $TOF_{Smax}$ of a maximum detected intensity ($I_{Smax}$) ultrasound signal transmitted between ultrasound imaging probe 13 and ultrasound transducer 15; and computes an out-of-plane distance $D_{op}$, between the ultrasound transducer 15 and image plane 12, based on the intensity $I_{Smax}$ and the time of flight $TOF_{Smax}$ of the maximum detected intensity $I_{Smax}$ ultrasound signal; wherein computing out-of-plane distance $D_{op}$, comprises comparing the maximum detected intensity $I_{Smax}$ with model MO describing an expected variation of in-plane maximum detected intensity $I_{SmaxInplane}$ with time of flight, at the time of flight $TOF_{Smax}$ of the maximum detected intensity $I_{Smax}$ ultrasound signal; and indicates the out-of-plane distance $D_{op}$, in the reconstructed ultrasound image RUI.

Figures 4A, 4B, 4C:
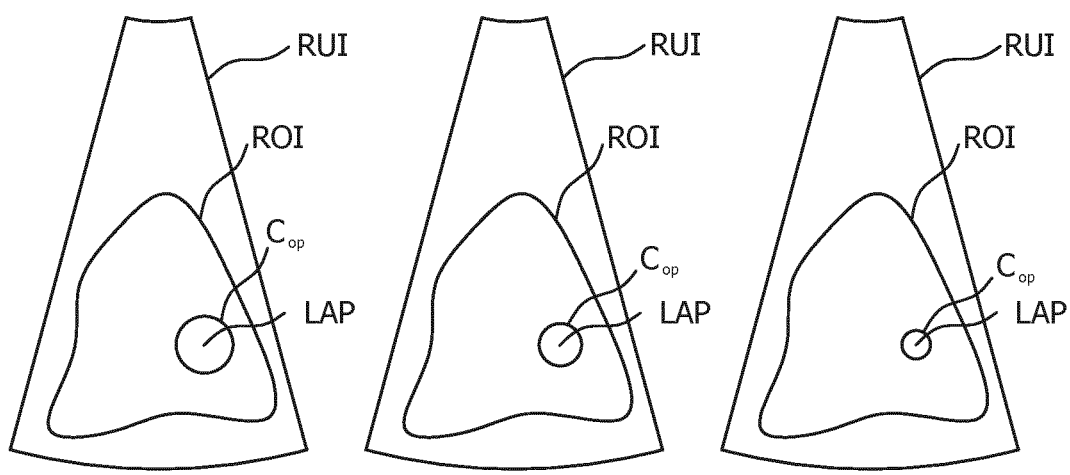
FIG. 4A, FIG. 4B, FIG. 4C each illustrate a reconstructed ultrasound image RUI that includes region of interest ROI and a first icon $C_{op}$ that is indicative of a circular zone with a radius corresponding to out-of-plane distance $D_{op}$.

In some exemplary implementations the out-of-plane distance $D_{op}$ may be indicated by means of a circular zone with a radius corresponding to the out-of-plane distance $D_{op}$. Thereto, FIG. 4A, FIG. 4B, FIG. 4C each illustrate a reconstructed ultrasound image RUI that includes region of interest ROI and a first icon $C_{op}$ that is indicative of a circular zone with a radius corresponding to out-of-plane distance $D_{op}$. With reference to FIG. 4, indicating the out-of-plane distance $D_{op}$, may include providing first icon $C_{op}$ at the computed lateral position $LAP_{TOFSmax, \theta IPA}$, the first icon $C_{op}$ being indicative of a circular zone with a radius corresponding to the out-of-plane distance $D_{op}$. FIG. 4 also indicates region of interest ROI and within which the lateral position LAP of ultrasound transducer 15 has been determined. In FIG. 4A ultrasound transducer 15 is some distance from image plane 12 as indicated by the radius of circle $C_{op}$. Ultrasound transducer 15 is moved closer to image plane 12 throughout FIG. 4B and FIG. 4C, resulting in a corresponding reduction in the radius of circle $C_{op}$. Whilst a circle is indicated in FIG. 4, other icons than a complete circle and which are likewise indicative of a circular zone may be used in the same manner, including e.g. a circular arrangement of dots or dashes, a circular arrangement of radially-directed lines or arrows, the tips of which indicate a circular zone, and so forth. The use of an icon at the computed position with a circular zone indicative of the out-of-plane distance indicates intuitively to a user whether the interventional device is being advanced towards or away-from the image plane based on whether the circle grows or shrinks This allows for improved guidance of the interventional device.

In some exemplary implementations the radius corresponding to out-of-plane distance $D_{op}$, is determined based on scaling the maximum detected intensity $I_{Smax}$ to the expected in-plane maximum detected intensity $I_{SmaxInplane}$, at the time of flight $TOF_{Smax}$ of the maximum detected intensity $I_{Smax}$ ultrasound signal. Thus, as described above with reference to FIG. 3, the radius of circle $C_{op}$ in FIG. 4 will change as ultrasound transducer 15 is moved towards and away from image plane 12.

As can be seen from FIG. 3, the maximum detected in-plane intensity $I_{SmaxInplane}$ typically reduces as the time of flight TOF increases. However the nature of this variation with out-of-plane distance may also depend upon the time of flight. Determining the radius based on scaling the maximum detected intensity $I_{Smax}$ to the expected in-plane maximum detected intensity $I_{SmaxInplane}$ results in a qualitative indication of the out-of-plane distance and circumvents issues surrounding out-of-plane variations in the intensity $I_{Smax}$. Such an indication is sufficient for a user to accurately navigate the interventional device to the image plane, and obviates the need for full three-dimensional calibration data that might otherwise be required to determine an exact out-of-plane distance, as well as the latency associated with searching such three-dimensional data to determine the out of-plane distance.

In some exemplary implementations the first icon $C_{op}$ has a perimeter and the appearance of the first icon $C_{op}$ is configured to change based on a comparison of the maximum detected intensity $I_{Smax}$ with the expected in-plane maximum detected intensity $I_{SmaxInplane}$, at the time of flight $TOF_{Smax}$ of the maximum detected intensity $I_{Smax}$ ultrasound signal. The appearance of the first icon $C_{op}$ may change by at least one of:

changing a color of the perimeter of the first icon $C_{op}$;
changing a contrast of the perimeter of the first icon $C_{op}$;
indicating the perimeter of the first icon $C_{op}$ with dots or dashes;
causing the perimeter of the first icon $C_{op}$ to pulse over time;
if i) a ratio of the maximum detected intensity $I_{Smax}$ to the expected in-plane maximum detected intensity $I_{SmaxInplane}$, at the time of flight $TOF_{Smax}$ of the maximum detected intensity $I_{Smax}$ ultrasound signal, or ii) the maximum detected intensity $I_{Smax}$, lies within a predetermined range. Other features of the icon may also be changed likewise, for example first icon $C_{op}$ may take the form of a partially-transparent circular zone, under these conditions.

Changing the appearance of the perimeter has the effect of indicating to a user the position of the interventional device at predetermined positions respective the imaging plane. This feature allows the rapid indication to a user of the general position of the interventional device respective the imaging plane. For example, the with reference to zones I-III in FIG. 3, a color of the icon may be green when the maximum detected intensity or its ratio indicates a value close to the expected in-plane maximum detected intensity, i.e. in zone I, and red for values within an abutting range, i.e. in zone II, and white for positions outside this range, i.e. in zone III.

In some exemplary implementations the radius corresponding to out-of-plane distance $D_{op}$ has a minimum value. Moreover, the position determination unit may limit the radius to the minimum value if i) a ratio of the maximum detected intensity $I_{Smax}$ to the expected in-plane maximum detected intensity $I_{SmaxInplane}$, at the time of flight $TOF_{Smax}$ of the maximum detected intensity $I_{Smax}$ ultrasound signal, or ii) the maximum detected intensity $I_{Smax}$, exceeds a predetermined value. The predetermined value may for example be 90 percent or 95 percent, or within a predetermined millivolt or milliwatt range, of the expected in-plane maximum detected intensity $I_{SmaxInplane}$.

A user is typically interested in positioning the interventional device in the imaging plane; and thus in this implementation first icon $C_{op}$ may for example be restricted to the minimum radius when the icon is within a predetermined range of exactly in the imaging plane. In so doing the user may to some extent relax their concentration when the interventional device is sufficiently well localized. This prevents the user from continually making minute adjustments of the position of the interventional device, allowing them to focus on other tasks.

In some exemplary implementations position determination unit PDU may suppress the provision of the first icon $C_{op}$ in reconstructed ultrasound image RUI if i) a ratio of the maximum detected intensity $I_{Smax}$ to the expected in-plane maximum detected intensity $I_{SmaxInplane}$, at the time of flight $TOF_{Smax}$ of the maximum detected intensity $I_{Smax}$ ultrasound signal, or ii) the maximum detected intensity $I_{Smax}$, falls below a predetermined value. If either of these parameters fall below the predetermined value the system may be insufficiently sensitive to reliably indicate the position of the interventional device respective the imaging plane. Weakly detected ultrasound signals may be confounded by electromagnetic interference or noise. Under such circumstances it is preferable to suppress the provision of the first icon in the reconstructed ultrasound image in order to avoid indicating a potentially inaccurate position.

Figures 5A, 5B, 5C:
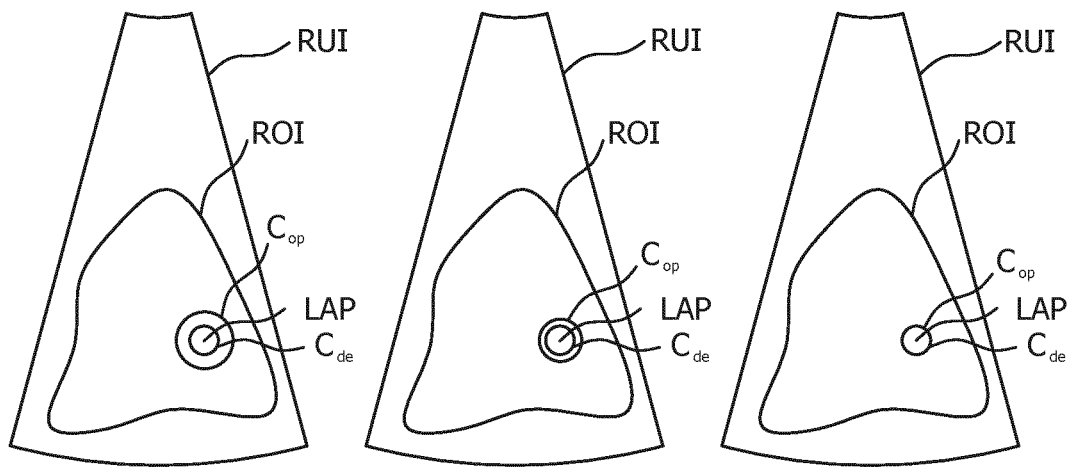

With reference to FIG. 5, in some exemplary implementations interventional device 11 includes a feature 11a. Thereto, FIG. 5A, FIG. 5B, FIG. 5C each illustrate a reconstructed ultrasound image RUI that includes a region of interest ROI, first icon $C_{op}$ and a co-centred second icon $C_{de}$ that is indicative of a circular zone with a radius corresponding to distance $L_p$ between ultrasound transducer 15 and interventional device feature 11a. As exemplified in FIG. 1 the feature may be its distal end 11a. Moreover, ultrasound transducer 15 is attached to interventional device 11 at a predetermined distance $L_p$ from interventional device feature 11a. In such implementations, position determination unit PDU provides a second icon $C_{de}$ in reconstructed ultrasound image RUI, the second icon $C_{de}$ being indicative of a circular zone with a radius corresponding to the predetermined distance $L_p$ between ultrasound transducer 15 and interventional device feature 11a. Moreover, first icon $C_{op}$ and second icon $C_{de}$ share a common center.

With reference to FIG. 5, in which ultrasound transducer 15 is progressively advanced towards image plane 12 from FIG. 5A-FIG. 5C, icon $C_{op}$ gradually decreases in size whilst second icon $C_{de}$ has a fixed size. In FIG. 5C the two icons overlap.

The second icon $C_{de}$ defines a portion of the image plane 12 corresponding to a range of possible positions of the interventional device feature 11a. As mentioned above, since the interventional device feature 11a is known to be on or within the perimeter of the circular zone defined by second icon $C_{de}$, improved positioning of the interventional device feature respective the image plane is provided. Put another way, a user of the system has confidence that the interventional device feature does not impact image features that lie outside this circular zone. Moreover, the localization can be provided using only a single ultrasound transducer, thereby simplifying manufacture of the interventional device.

The position of alternative features of an interventional device 11 may be indicated in a similar manner, such as, and without limitation, a biopsy sampling point of the interventional device, a cutting edge of the interventional device, an opening of a channel in the interventional device, a sensor (e.g. for sensing flow, pressure, temperature etc.) of the interventional device, a surgical tool (e.g. a scraper) integrated in the interventional device, a drug delivery point of the interventional device, or an energy delivery point of the interventional device.

Figure 6:
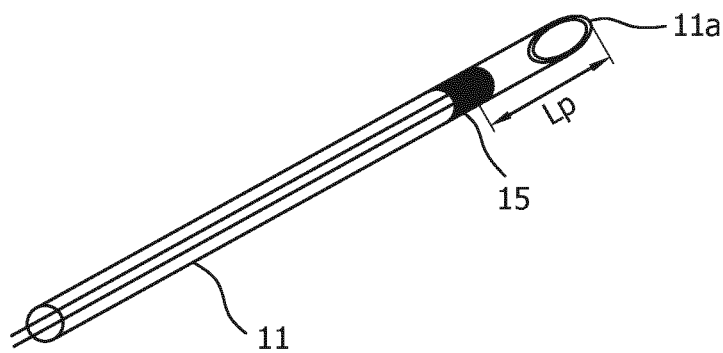
FIG. 6 illustrates an interventional device 11 that is suitable for use with system 10.

In this respect, FIG. 6 illustrates an interventional device 11 that is suitable for use within system 10. Ultrasound transducer 15 is attached at a predetermined distance $L_p$ from a feature, i.e. distal end 11a of interventional device 11. Ultrasound transducer 15 may be attached to interventional device 11 by various means including using an adhesive. Electrical conductors that carry electrical signals from ultrasound transducer 11 to position determination unit PDU are also shown, although as mentioned above it is contemplated to alternatively use a wireless link to communicate the transducer signals with position determination unit PDU.

Ultrasound transducer 15 described above with reference to FIG. 1, FIG. 2 and FIG. 6 may be provided by a variety of piezoelectric materials. Both hard and soft piezoelectric materials are suitable. Micromachined Electromechanical Structures, i.e. MEMS devices such as Capacitive Micromachined Ultrasound Transducers, i.e. CMUT, devices are also suitable. When the ultrasound transducer is a detector, preferably it is formed from Polyvinylidene fluoride, otherwise known as PVDF whose mechanical properties and manufacturing processes lend themselves to attachment to curved surfaces such as medical needles. Alternative materials include a PVDF co-polymer such as polyvinylidene fluoride trifluoroethylene, a PVDF ter-polymer such as P(VDF-TrFE-CTFE). Preferably the ultrasound transducer is wrapped around an axis of the interventional device in order to provide sensing around 360 degrees of rotation about the axis although this need not always be the case.

In some exemplary implementations position determination unit PDU may cause the appearance of first icon $C_{op}$ and/or second icon $C_{de}$ to change when the out-of-plane distance $D_{op}$ is less than or equal to the predetermined distance $L_p$. During the contemplated procedures, a user is principally interested in positioning feature 11a of the interventional device in the image plane. Thus when the maximum detected intensity $I_{Smax}$ corresponds to an estimated out of plane distance $D_{op}=L_p$, the change in appearance of first icon $C_{op}$ and/or second icon $C_{de}$ alerts the user to this situation. In so doing, during for example an out-of-plane procedure, a user is alerted to the fact that the interventional device feature is in the center of the image plane by the appearance change. The first icon $C_{op}$ and the second icon $C_{de}$ may exemplarily, each have a perimeter. Moreover, the appearance of at least one of the first icon $C_{op}$ and the second icon $C_{de}$ may change by at least one of: changing a color of the perimeter of the first icon $C_{op}$ or the second icon $C_{de}$; changing a contrast of the perimeter of the first icon $C_{op}$ or the second icon $C_{de}$; indicating the perimeter of the first icon $C_{op}$ or the second icon $C_{de}$ with dots or dashes; causing the perimeter of the first icon $C_{op}$ or the second icon $C_{de}$ to pulse over time; causing the first icon $C_{op}$ and the second icon $C_{de}$ to merge into a common icon; suppressing the provision of the first icon $C_{op}$ or the second icon $C_{de}$ in the reconstructed ultrasound image RUI.

In some exemplary implementations the radius of the first icon $C_{op}$ has a minimum value that is equal to the radius of the second icon $C_{de}$ and the radius of the first icon $C_{op}$ may be limited to the minimum value when the out-of-plane distance $D_{op}$, is less than or equal to the predetermined distance L. By so limiting the size of the first icon as the interventional device approaches the image plane, as described above, in an out-of-plane procedure a user may to some extent relax their concentration when the minimum size is reached knowing that, sufficient positioning accuracy has been reached.

Figure 7:
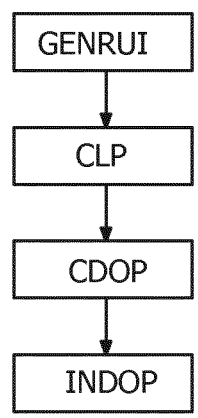
FIG. 7 illustrates various method steps of a method that may be used with system 10.

FIG. 7 illustrates various method steps of a method that may be used with system 10. With reference to FIG. 7 a method of determining a position of interventional device 11 respective image plane 12 defined by ultrasound imaging probe 13 of beamforming ultrasound imaging system 14 in which the position of interventional device 11 is determined based on ultrasound signals transmitted between ultrasound imaging probe 13 and ultrasound transducer 15 attached to interventional device 11; includes the steps of:

- generating GENRUI a reconstructed ultrasound image RUI corresponding to an image plane 12 defined by the ultrasound imaging probe 13;
- computing CLP a lateral position $LAP_{TOFSmax, \theta IPA}$ of the ultrasound transducer respective the image plane 12 based on a time of flight $TOF_{Smax}$ of a maximum detected intensity $I_{Smax}$ ultrasound signal of the ultrasound signals transmitted between the ultrasound imaging probe 13 and the ultrasound transducer 15;
- computing CDOP an out-of-plane distance $D_{op}$, between the ultrasound transducer 15 and the image plane 12, based on the intensity $I_{Smax}$ and the time of flight $TOF_{Smax}$ of the maximum detected intensity $I_{Smax}$ ultrasound signal; wherein computing the out-of-plane distance comprises comparing the maximum detected intensity $I_{Smax}$ with a model describing an expected variation of in-plane maximum detected intensity $I_{SmaxInplane}$ with time of flight, at the time of flight $TOF_{Smax}$ of the maximum detected intensity $I_{Smax}$ ultrasound signal; and indicating INDOP the out-of-plane distance $D_{op}$ in the reconstructed ultrasound image RUI.

It is to be noted that other implementations of the method may additionally incorporate one or more aspects described with respect to an implementation of the system.

The method steps illustrated in FIG. 7, optionally including other method steps described herein, may be stored on a computer program product as instructions that are executable by a processor. The computer program product may be provided by dedicated hardware, or hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk—read only memory "CD-ROM", compact disk—read/write "CD-R/W", Blu-Ray™ and DVD.

In this respect, a computer program product is also provided for use with system 10. The computer program product includes instructions which when executed on a processor of system 10 for determining a position of an interventional device 11 respective an image plane 12 defined by an ultrasound imaging probe 13 of a beamforming ultrasound imaging system 14 in which the position of the interventional device 11 is determined based on ultrasound signals transmitted between the ultrasound imaging probe 13 and an ultrasound transducer 15 attached to the interventional device 11; causes the processor to carry out the aforementioned method steps.

In summary, a system has been described for determining a position of an interventional device respective an image plane defined by an ultrasound imaging probe of a beamforming ultrasound imaging system in which the position of the interventional device is determined based on ultrasound signals transmitted between the ultrasound imaging probe and an ultrasound transducer attached to the interventional device. The system includes an image reconstruction unit and a position determination unit. The image reconstruction unit provides a reconstructed ultrasound image corresponding to an image plane defined by the ultrasound imaging probe. The position determination unit computes a lateral position of the ultrasound transducer respective the image plane based on a time of flight of a maximum detected intensity ultrasound signal transmitted between the ultrasound imaging probe and the ultrasound transducer. The position determination unit also computes an out-of-plane distance between the ultrasound transducer and the image plane, based on the intensity and the time of flight of the maximum detected intensity ultrasound signal. Computing the out-of-plane distance involves comparing the maximum detected intensity with a model describing an expected variation of in-plane maximum detected intensity with time of flight, at the time of flight of the maximum detected intensity ultrasound signal. The position determination unit also indicates the out-of-plane distance in the reconstructed ultrasound image. Whilst the invention has been illustrated and described in detail in the drawings and foregoing description in relation to a medical needle, such illustrations and descriptions are to be considered illustrative or exemplary and not restrictive. Any reference signs in the claims should not be construed as limiting the scope of the invention. Moreover it is to be understood that the various examples, implementations and embodiments illustrated herein may be combined in order to provide various systems and methods for determining a position of an interventional device respective an image plane of a beamforming ultrasound imaging system.

As used herein, the term "or" should be interpreted as a disjunctive "or." Further, the term "or" and the term "and" when prefaced by the term "at least one of" or the term by "one or more of" should be interpreted as a disjunctive list such that, for example, a list of "at least one of A or B" or a list of "one or more of A and B" or a list of "A or B" should be interpreted to include either A or B, one of A and one of B, a combination of one or more of each of A and B, both A and B, or combinations of one or more of A and B, and such other combinations as relevant to the recited list or terms consistent with the corresponding description in the specification.

The invention claimed is:

1. A system for determining a position of an interventional device, the system comprising:
   an image reconstruction processor configured to reconstruct an ultrasound image corresponding to an image plane defined by an ultrasound imaging probe; and
   a position determination processor configured to:
   receive a model defining an expected variation of in-plane maximum intensity of a signal only as a function of time of flight of the signal, detect a maximum intensity ultrasound signal transmitted between the ultrasound imaging probe and an ultrasound transducer attached to the interventional device and detect an intensity of the maximum intensity ultrasound signal,
   compute a lateral position of the ultrasound transducer relative to the image plane based on a time of flight of the maximum intensity ultrasound signal,
   search the model in only one dimension to determine an expected in-plane maximum intensity for the maximum intensity ultrasound signal, wherein the one dimension is the time of flight of the maximum intensity ultrasound signal,
   compute an out-of-plane distance between the ultrasound transducer and the image plane based on a comparison of the intensity of the maximum intensity ultrasound signal and the expected in-plane maximum intensity for the maximum intensity ultrasound signal,
   determine the position of an interventional device relative to the image plane based on the out-of-plane distance and the lateral position, and
   indicate the out-of-plane distance in the reconstructed ultrasound image.

2. The system according to claim 1, wherein, to indicate the out-of-plane distance, the position determination processor is further configured to provide a first icon at the lateral position, wherein the first icon is indicative of a circular zone with a radius corresponding to the out-of-plane distance.

3. The system according to claim 2, wherein the position determination processor is further configured to determine the radius based on scaling the intensity of the maximum intensity ultrasound signal to the expected in-plane maximum intensity at the time of flight of the maximum intensity ultrasound signal.

4. The system according to claim 2, wherein the first icon includes a perimeter, and wherein the position determination processor is further configured to change an appearance of the first icon based on a comparison of the intensity of the maximum intensity ultrasound signal with the expected in-plane maximum intensity at the time of flight of the maximum intensity ultrasound signal, wherein the position determination processor is configured to change the appearance of the first icon by changing at least one of:
   a color of the perimeter of the first icon;
   a contrast of the perimeter of the first icon;
   an indication of the perimeter of the first icon; or
   a pulsing over time of the perimeter of the first icon, and
   wherein the position determination processor is further configured to change the appearance of the first icon if i) a ratio of the intensity of the maximum intensity ultrasound signal to the expected in-plane maximum intensity at the time of flight of the maximum intensity ultrasound signal or ii) the intensity of the maximum intensity ultrasound signal lies within a predetermined range.

5. The system according to claim 2, wherein the radius has a minimum value, and wherein the position determination processor is further configured to limit the radius to the minimum value if i) a ratio of the intensity of the maximum intensity ultrasound signal to an expected in-plane maximum intensity at the time of flight of the maximum intensity ultrasound signal or ii) the intensity of the maximum intensity ultrasound signal exceeds a predetermined value.

6. The system according to claim 2, wherein the position determination processor is further configured to suppress a provision of the first icon in the reconstructed ultrasound image if i) a ratio of the intensity of the maximum intensity ultrasound signal to the expected in-plane maximum intensity at the time of flight of the maximum intensity ultrasound signal, or ii) the intensity of the maximum intensity ultrasound signal falls below a predetermined value.

7. The system according to claim 2, wherein the interventional device includes a reference point, and wherein the ultrasound transducer is attached to the interventional device at a predetermined distance from the reference point,
   wherein the position determination processor is further configured to provide a second icon in the reconstructed ultrasound image, the second icon being indicative of a circular zone with a radius corresponding to the predetermined distance between the ultrasound transducer and the reference point, and
   wherein the first icon and the second icon share a common center.

8. The system according to claim 7, wherein the second icon defines a portion of the image plane corresponding to a range of possible positions of the reference point.

9. The system according to claim 7, wherein the reference point is one of the following:
   a distal end of the interventional device;
   an opening of a channel in the interventional device;
   a biopsy sampling point of the interventional device;
   a cutting edge of the interventional device;
   a sensor of the interventional device;
   a surgical tool integrated into the interventional device;
   a drug delivery point of the interventional device; or
   an energy delivery point of the interventional device.

10. The system according to claim 7, wherein the position determination processor is further configured to cause an appearance of at least one of the first icon and the second icon to change when the out-of-plane distance is less than or equal to the predetermined distance.

11. The system according to claim 10, wherein the first icon and the second icon each have a perimeter, and wherein the position determination processor is further configured to change an appearance of at least one of the first icon and the second icon by changing at least one of a color of the perimeter of the first icon or the second icon;
   a contrast of the perimeter of the first icon or the second icon;
   an indication of the perimeter of the first icon or the second icon;
   a pulsing over time of the perimeter of the first icon or the second icon;
   a merging of the first icon and the second icon; or
   a suppression of the provision of the first icon or the second icon in the reconstructed ultrasound image.

12. The system according to claim 7, wherein the radius of the first icon has a minimum value that is equal to the radius of the second icon, and wherein the radius of the first icon is limited to the minimum value when the out-of-plane distance is less than or equal to the predetermined distance.

13. The system according to claim 1, further comprising the interventional device with the ultrasound transducer attached thereto.

14. A method of determining a position of an interventional device, the method comprising:
generating a reconstructed ultrasound image corresponding to an image plane defined by an ultrasound imaging probe;
receiving a model defining an expected variation of in-plane maximum intensity of a signal only as a function of time of flight of the signal;
detecting a maximum intensity ultrasound signal transmitted between the ultrasound imaging probe and an ultrasound transducer attached to the interventional device and detecting an intensity of the maximum intensity ultrasound signal;
computing a lateral position of the ultrasound transducer relative to the image plane based on a time of flight of the maximum intensity ultrasound signal;
searching the model in only one dimension to determine an expected in-plane maximum intensity for the maximum intensity ultrasound signal, wherein the one dimension is the time of flight of the maximum intensity ultrasound signal;
computing an out-of-plane distance between the ultrasound transducer and the image plane based on a comparison of the intensity of the maximum intensity ultrasound signal and the expected in-plane maximum intensity for the maximum intensity ultrasound signal;
determining the position of an interventional device relative to the image plane based on the out-of-plane distance and the lateral position; and
indicating the out-of-plane distance in the reconstructed ultrasound image.

15. The method according to claim 14, wherein indicating the out-of- plane distance comprises providing a first icon at the lateral position, the first icon being indicative of a circular zone with a radius corresponding to the out-of-plane distance.

16. The method according to claim 15, wherein the radius is determined based on scaling the intensity of the maximum intensity ultrasound signal to the expected in-plane maximum intensity at the time of flight of the maximum intensity ultrasound signal.

17. The method according to claim 15, wherein the first icon includes a perimeter, and the method further comprises changing the appearance of the first icon based on a comparison of the intensity of the maximum intensity ultrasound signal with the expected in-plane maximum intensity at the time of flight of the maximum intensity ultrasound signal.

18. The method according to claim 15, wherein the radius has a minimum value, and the method further comprises limiting the radius to the minimum value if i) a ratio of the intensity of the maximum intensity ultrasound signal to the expected in-plane maximum intensity at the time of flight of the maximum intensity ultrasound signal or ii) the intensity of the maximum intensity ultrasound signal exceeds a predetermined value.

19. The method according to claim 15, further comprising suppressing a provision of the first icon in the reconstructed ultrasound image if i) a ratio of the intensity of the maximum intensity ultrasound signal to the expected in-plane maximum intensity at the time of flight of the maximum intensity ultrasound signal or ii) the intensity of the maximum intensity ultrasound signal falls below a predetermined value.

20. A non-transitory computer readable medium having stored thereon instructions for determining a position of an interventional device, the instructions, when executed by a processor, cause the processor to:
generate a reconstructed ultrasound image corresponding to the an image plane defined by an ultrasound imaging probe;
receive a model defining an expected variation of in-plane maximum intensity of a signal only as a function of time of flight of the signal;
detect a maximum intensity ultrasound signal transmitted between the ultrasound imaging probe and an ultrasound transducer attached to the interventional device and detect intensity of the maximum intensity ultrasound signal;
compute a lateral position of the ultrasound transducer relative to the image plane based on a time of flight of the maximum detected intensity ultrasound signal;
search the model in only one dimension to determine an expected in-plane maximum intensity for the maximum intensity ultrasound signal, wherein the one dimension is the time of flight of the maximum intensity ultrasound signal;
compute an out-of-plane distance between the ultrasound transducer and the image plane based on a comparison of the intensity of the maximum intensity ultrasound signal and the expected in-plane maximum intensity for the maximum intensity ultrasound signal;
determine the position of an interventional device relative to the image plane based on the out-of-plane distance and the lateral position; and
indicate the out-of-plane distance in the reconstructed ultrasound image.

* * * * *